US011589837B2

(12) United States Patent
Saito

(10) Patent No.: US 11,589,837 B2
(45) Date of Patent: Feb. 28, 2023

(54) ULTRASOUND TRANSDUCER, ULTRASOUND ENDOSCOPE, AND METHOD OF MANUFACTURING ULTRASOUND TRANSDUCER

(71) Applicant: OLYMPUS CORPORATION, Tokyo (JP)

(72) Inventor: Miku Saito, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 563 days.

(21) Appl. No.: 16/653,087

(22) Filed: Oct. 15, 2019

(65) Prior Publication Data

US 2020/0046319 A1    Feb. 13, 2020

Related U.S. Application Data

(63) Continuation of application No. PCT/JP2018/014424, filed on Apr. 4, 2018.

(30) Foreign Application Priority Data

Apr. 18, 2017   (JP) .............................. JP2017-082069

(51) Int. Cl.
*A61B 8/00*     (2006.01)
*A61B 8/12*     (2006.01)
(Continued)

(52) U.S. Cl.
CPC ................ *A61B 8/445* (2013.01); *A61B 8/12* (2013.01); *A61B 8/4494* (2013.01);
(Continued)

(58) Field of Classification Search
CPC ......... A61B 8/445; A61B 8/4494; A61B 8/12; B06B 1/0625; B06B 2201/76;
(Continued)

(56) References Cited

U.S. PATENT DOCUMENTS

2002/0062082 A1    5/2002   Ohara et al.
2006/0058676 A1    3/2006   Yagi et al.
(Continued)

FOREIGN PATENT DOCUMENTS

JP    H04-166139 A    6/1992
JP    H05-042146 A    2/1993
(Continued)

OTHER PUBLICATIONS

Japanese Office Action dated Aug. 25, 2020 in Japanese Patent Application No. 2017-082069.
International Search Report dated Jun. 12, 2018 issued in PCT/JP2018/014424.

*Primary Examiner* — Colin T. Sakamoto
*Assistant Examiner* — Tommy T Ly
(74) *Attorney, Agent, or Firm* — Scully, Scott, Murphy & Presser, P.C.

(57) ABSTRACT

A radial type ultrasound transducer is arranged in an ultrasound endoscope including a bending portion on a distal end side of an insertion portion. The ultrasound transducer includes: a plurality of piezoelectric elements arranged at predetermined intervals in a circumferential manner and configured to transmit and receive ultrasound waves; a plurality of electrodes arranged in the respective piezoelectric elements; and a flexible printed circuit electrically connected to each of the electrodes. The flexible printed circuit includes a plurality of wires that extend such that at least parts of the wires cross a direction perpendicular to an arrangement direction of the piezoelectric elements, and the plurality of wires are electrically connected to the respective electrodes of the piezoelectric elements at positions where at least parts of the wires cross the direction perpendicular to the arrangement direction of the piezoelectric elements.

11 Claims, 12 Drawing Sheets

(51) Int. Cl.
*B06B 1/06* (2006.01)
*H01L 41/047* (2006.01)
*H01L 41/29* (2013.01)
*H01L 41/338* (2013.01)

(52) U.S. Cl.
CPC ........ *B06B 1/0625* (2013.01); *H01L 41/0475* (2013.01); *H01L 41/29* (2013.01); *H01L 41/338* (2013.01); *B06B 2201/76* (2013.01)

(58) Field of Classification Search
CPC ... B06B 1/0633; H01L 41/0475; H01L 41/29; H01L 41/338

See application file for complete search history.

(56) References Cited

U.S. PATENT DOCUMENTS

| | | | |
|---|---|---|---|
| 2011/0245681 A1* | 10/2011 | Hasegawa | A61B 8/12 600/459 |
| 2013/0188446 A1* | 7/2013 | Kubota | G03B 42/06 367/7 |

FOREIGN PATENT DOCUMENTS

| | | | |
|---|---|---|---|
| JP | 2002-153468 A | | 5/2002 |
| JP | 2002-153469 A | | 5/2002 |
| JP | 2003-033354 A | | 2/2003 |
| JP | 2008-237842 A | | 10/2008 |
| JP | 2008237842 A | * | 10/2008 |

\* cited by examiner

ULTRASOUND TRANSDUCER, ULTRASOUND ENDOSCOPE, AND METHOD OF MANUFACTURING ULTRASOUND TRANSDUCER

This application is a continuation of PCT International Application No. PCT/JP2018/014424 filed on Apr. 4, 2018, which designates the United States, incorporated herein by reference, and which claims the benefit of priority from Japanese Patent Application No. 2017-082069, filed on Apr. 18, 2017, incorporated herein by reference.

BACKGROUND

The present disclosure relates to an ultrasound transducer, an ultrasound endoscope, and a method of manufacturing the ultrasound transducer.

In the related art, an ultrasound endoscope that inserts a flexible elongated insertion portion into a subject, such as a human being, and observes the inside of the subject by using an ultrasound transducer disposed at a distal end of the insertion portion has been known. In addition, as the ultrasound transducer, a radial type ultrasound transducer in which a plurality of piezoelectric elements are arranged at predetermined pitch intervals in a circumferential manner has been known (see, for example, Japanese Patent Laid-open Publication No. H5-42146 and Japanese Patent Laid-open Publication No. H4-166139).

A plurality of electrodes are electrically connected to the respective piezoelectric elements. Further, a flexible printed circuit (FPC) is fixed to a proximal end side of the electrodes, and a plurality of wires printed on the FPC are electrically connected to the respective electrodes.

Furthermore, a certain ultrasound endoscope includes a distal end rigid portion, which is made of a rigid member, which is disposed on a distal end of an insertion portion to be inserted into a subject, and which houses piezoelectric elements, and a bending portion, which is arranged on a proximal end side of the distal end rigid portion and which is bent in accordance with operation on an operating unit that is arranged on a proximal end side of the insertion portion.

SUMMARY

According to one aspect of the present disclosure, there is provided a radial type ultrasound transducer arranged in an ultrasound endoscope including a bending portion on a distal end side of an insertion portion, the ultrasound transducer including: a plurality of piezoelectric elements arranged at predetermined intervals in a circumferential manner and configured to transmit and receive ultrasound waves; a plurality of electrodes arranged in the respective piezoelectric elements; and a flexible printed circuit electrically connected to each of the electrodes, wherein the flexible printed circuit includes a plurality of wires that extend such that at least parts of the wires cross a direction perpendicular to an arrangement direction of the piezoelectric elements, and the plurality of wires are electrically connected to the respective electrodes of the piezoelectric elements at positions where at least parts of the wires cross the direction perpendicular to the arrangement direction of the piezoelectric elements.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of an ultrasound transducer, an ultrasound endoscope, and a method of manufacturing the ultrasound transducer according to the present disclosure will be described below with reference to the drawings. The present disclosure is not limited by the embodiments below. The present disclosure is generally applicable to a radial type ultrasound transducer, an ultrasound endoscope, and a method of manufacturing the ultrasound transducer.

Further, in the description of the drawings, the same or corresponding components are denoted by the same reference symbols appropriately. Furthermore, it is necessary to note that the drawings are schematic, and dimensional relations among the components, ratios among the components, and the like may be different from the actual ones. Moreover, the drawings may include portions that have different dimensional relations or ratios.

Embodiment

Figure 1:
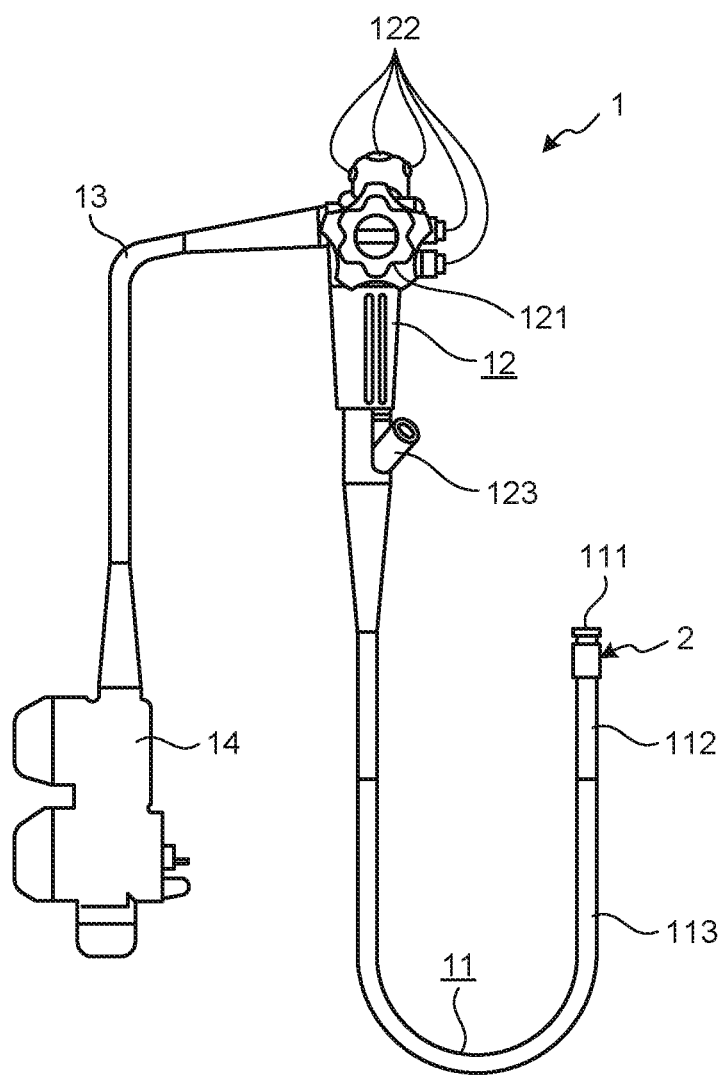
FIG. 1 is a schematic diagram illustrating an ultrasound endoscope including an ultrasound transducer according to an embodiment.

FIG. 1 is a schematic diagram illustrating an ultrasound endoscope including an ultrasound transducer according to an embodiment. An ultrasound endoscope 1, in a distal end portion thereof, converts an electrical pulse signal received from an ultrasound observation device into an ultrasound pulse (acoustic pulse), applies the ultrasound pulse to a subject, converts an ultrasound echo reflected by the subject into an electrical echo signal that represents the ultrasound echo by a voltage change, and outputs the echo signal.

The ultrasound endoscope 1 generally includes an imaging optical system and an imaging element, is inserted into a digestive tract (an esophagus, a stomach, a duodenum, or a large intestine) or a respiratory organ (a trachea or a bronchus) of the subject, and is able to capture images of the digestive tract or the respiratory organ. Further, the ultrasound endoscope 1 is able to capture images of a surrounding organ (a pancreas, a gallbladder, a bile duct, a biliary tract, lymph nodes, a mediastinal organ, a blood vessel, or the like) by using ultrasound waves. Furthermore, the ultrasound endoscope 1 includes a light guide that guides illumination light to be applied to the subject at the time of optical imaging. A distal end portion of the light guide reaches a distal end of an insertion portion of the ultrasound endoscope 1 to be inserted in the subject, and a proximal end portion of the light guide is connected to a light source device that emits the illumination light.

As illustrated in FIG. 1, the ultrasound endoscope 1 includes an insertion portion 11, an operating unit 12, a universal cable 13, and a connector 14.

The insertion portion 11 is a portion to be inserted into the subject. As illustrated in FIG. 1, the insertion portion 11 includes an ultrasound transducer 2 that is disposed on the distal end thereof, a distal end rigid portion 111 that houses a part of the ultrasound transducer 2, a bending portion 112 that is arranged on a proximal end side of the distal end rigid portion 111 and that is bent in accordance with operation on the operating unit 12, and a flexible tube portion 113 that is connected to a proximal end side of the bending portion 112 and that has flexibility. While details are not illustrated in the figures, in the insertion portion 11, the light guide that transmits illumination light supplied from the light source device and a plurality of signal cables for transmitting various signals are arranged and a treatment tool insertion path for inserting a treatment tool is formed.

The operating unit 12 is a portion that is arranged on a proximal end side of the insertion portion 11 and receives various kinds of operation from a doctor or the like. As illustrated in FIG. 1, the operating unit 12 includes a bending knob 121 for receiving operation of bending the bending portion 112 and a plurality of operating members 122 for performing various kinds of operation. Further, the operating unit 12 includes a treatment tool insertion opening 123 that communicates with the treatment tool insertion path and allows a treatment tool to be inserted into the treatment tool insertion path.

The universal cable 13 is a cable which extends from the operating unit 12 and in which a plurality of signal cables for transmitting various signals, an optical fiber for transmitting the illumination light supplied from the light source device, and the like are arranged.

The connector 14 is disposed on a distal end of the universal cable 13. The connector 14 is connected to the ultrasound observation device, an endoscope observation device, and the light source device via various cables.

The ultrasound transducer 2 is a radial type ultrasound transducer. A plurality of piezoelectric elements are arranged in a circumferentially-arrayed manner as the ultrasound transducer 2, and the ultrasound endoscope 1 causes the ultrasound transducer 2 to electronically perform scanning by electronically switching among the piezoelectric elements involved in transmission and reception of ultrasound waves or delaying transmission and reception of ultrasound waves in each of the piezoelectric elements.

Figure 2:
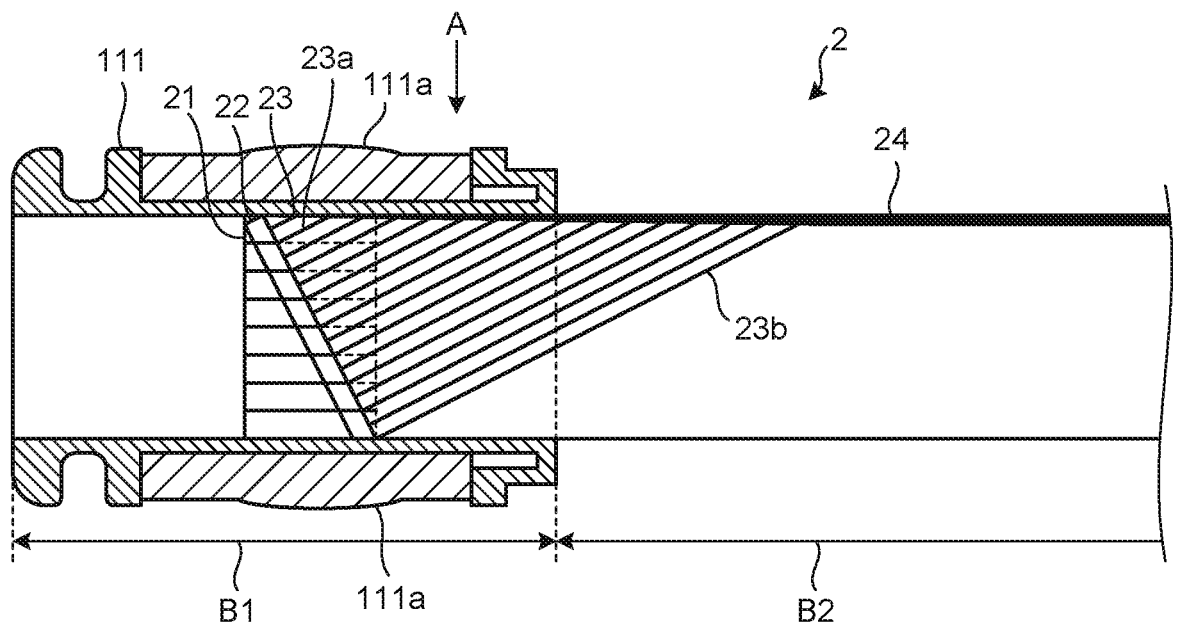
FIG. 2 is a partial cutaway diagram of a distal end of an insertion portion of the ultrasound endoscope illustrated in FIG. 1.
Figure 3:
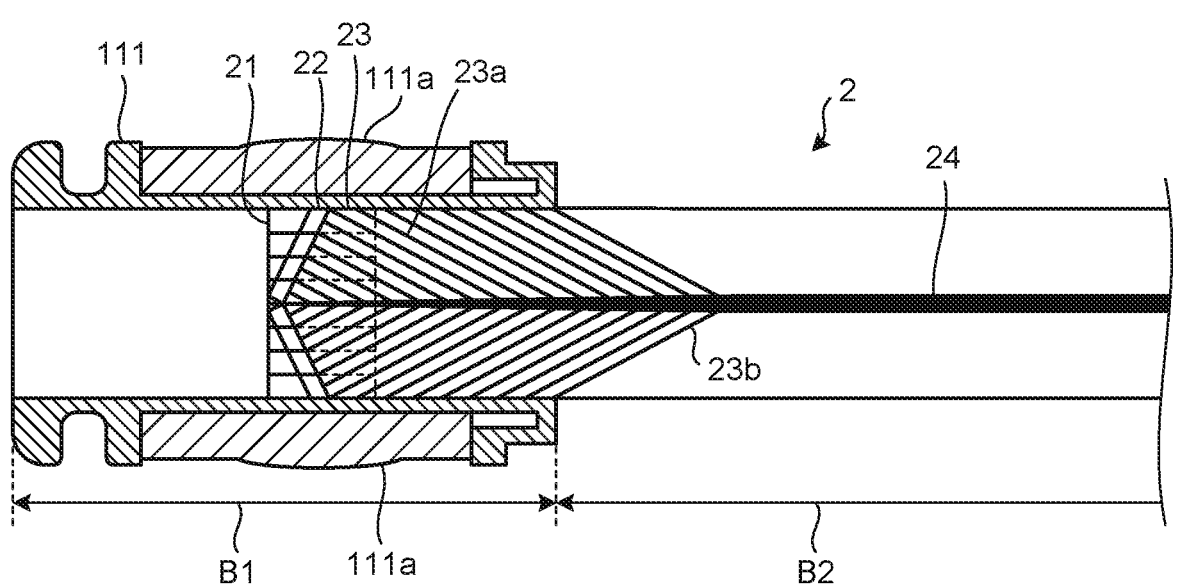
FIG. 3 illustrates the ultrasound transducer when viewed from a direction of arrow A in FIG. 2.

FIG. 2 is a partial cutaway diagram of the distal end of the insertion portion of the ultrasound endoscope illustrated in FIG. 1. FIG. 3 illustrates the ultrasound transducer when viewed from a direction of arrow A in FIG. 2. As illustrated in FIG. 2 and FIG. 3, the ultrasound transducer 2 includes a plurality of piezoelectric elements 21 that are arranged at predetermined pitch intervals in a circumferential manner and that transmit and receive ultrasound waves, a plurality of electrodes 22 that are arranged in the respective piezoelectric elements 21, an FPC 23 serving as a flexible printed circuit on which a plurality of wires 23a are printed and which is fixed on a proximal end side of the plurality of electrodes 22, and a plurality of lead wires 24 that are electrically connected to the respective wires 23a.

The piezoelectric elements 21 are housed in the distal end rigid portion 111, and transmit and receive ultrasound waves via an acoustic lens 111a that is disposed on an outer periphery of the distal end rigid portion 111. A portion B1 including the distal end rigid portion 111 is a portion that is not bendable in the distal end of the insertion portion 11. The piezoelectric elements 21 are arranged along an arrangement direction that is perpendicular to a direction in which the insertion portion 11 is extended. The piezoelectric elements 21 convert electrical pulse signals into acoustic pulses, apply the acoustic pulses to a subject, converts ultrasound echoes reflected by the subject into electrical echo signals that represent the ultrasound echoes by voltage changes, and output the echo signals.

The piezoelectric elements 21 are constructed with lead zirconate titanate (PZT) ceramic material, a PMN-PT single crystal, a PMN-PZT single crystal, a PZN-PT single crystal, a PIN-PZN-PT single crystal, or a relaxer material. The PMN-PT single crystal is an abbreviation of a solid solution of lead magnesium niobate and lead titanate. The PMN-PZT single crystal is an abbreviation of a solid solution of lead magnesium niobate and lead zirconate titanate. The PZN-PT single crystal is an abbreviation of a solid solution of lead zinc niobate and lead titanate. The PIN-PZN-PT single crystal is an abbreviation of a solid solution of lead indium niobate, lead zinc niobate, and lead titanate. The relaxer material is a generic term of a three-component piezoelectric material that is obtained by adding lead-based complex perovskite that is a relaxer material to PZT in order to increase a piezoelectric constant or permittivity. The lead-based complex perovskite is represented by $Pb(B1, B2)O_3$, where B1 is any of magnesium, zinc, indium, and scandium, and B2 is any of niobium, tantalum, and tungsten. These materials have excellent piezoelectric effects. Therefore, these materials make it possible to reduce an electrical impedance value even when the size of a device is reduced, and are preferable from the viewpoint of impedance matching with film electrodes arranged in the piezoelectric elements 21.

The single electrode 22 is electrically connected to an inner periphery of each of the piezoelectric elements 21. In each of FIG. 2 and subsequent drawings, the piezoelectric elements 21 on the outer side are indicated by dashed lines in order to explain inner configurations of the piezoelectric elements 21. Further, a ground electrode (not illustrated) for grounding is arranged on an outer periphery of each of the piezoelectric elements 21.

Figure 4:
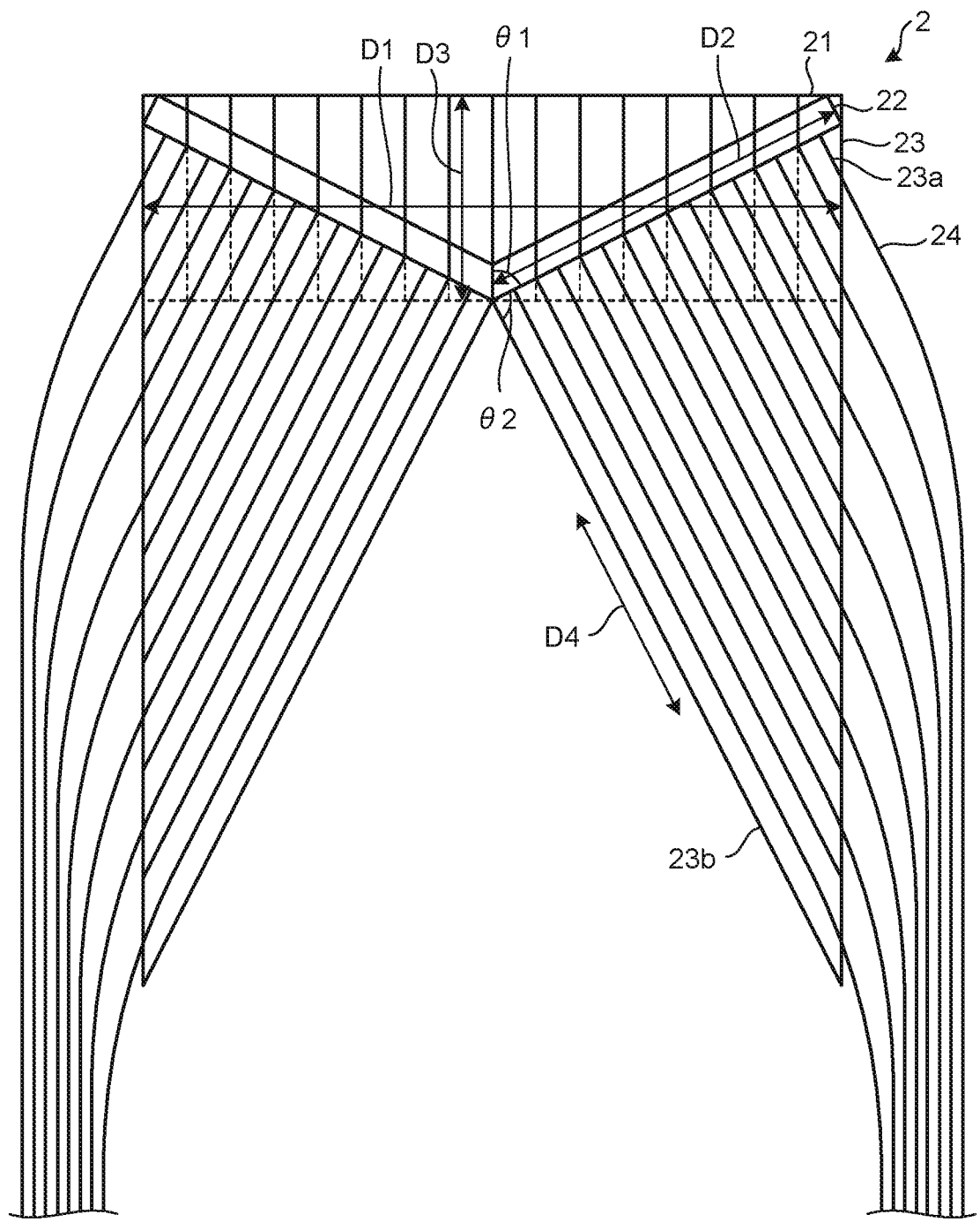
FIG. 4 illustrates a state before the ultrasound transducer illustrated in FIG. 2 is arranged in a circumferential manner.

FIG. 4 illustrates a state before the ultrasound transducer illustrated in FIG. 2 is arranged in a circumferential manner.

By rolling up, in a circumferential manner, the ultrasound transducer 2 in a planar state as illustrated in FIG. 4 such that the piezoelectric elements 21 are arranged on the outer side, the radial type ultrasound transducer 2 as illustrated in FIG. 2 and FIG. 3 is obtained. The plurality of electrodes 22 are arranged along a direction D2 that crosses an arrangement direction D1 of the piezoelectric elements 21. The electrodes 22 and the ground electrodes are made of metal or resin with conductivity.

The FPC 23 is fixed to the proximal end side of the electrodes 22 by soldering the electrodes 22 and the wires 23a. The FPC 23 is made of, for example, film resin and has flexibility. The FPC 23 has a hypotenuse 23b that obliquely extends from a proximal end side (lower side in FIG. 4) along a direction D4 crossing the direction D3 that is perpendicular to the arrangement direction D1 of the piezoelectric elements 21. Therefore, as illustrated in FIG. 2 and FIG. 3, in a portion in which the FPC 23 protrudes from the distal end rigid portion 111, the FPC 23 covers only a part of the insertion portion 11 that has a circular cross section, so that this portion has adequate flexibility. Consequently, a portion that can be bent in the distal end of the insertion portion 11 is a portion B2.

Referring back to FIG. 4, the plurality of wires 23a are electrically connected to the respective electrodes 22 and extend along the direction D4 crossing the direction D3 that is perpendicular to the arrangement direction D1 of the piezoelectric elements 21. More specifically, the plurality of wires 23a are arranged such that an angle θ1 between the direction D2 along which the plurality of electrodes 22 are arranged and the direction D3 that is perpendicular to the arrangement direction D1 of the piezoelectric elements 21 and an angle θ2 between the direction D2 along which the plurality of electrodes 22 are arranged and the direction D4 along which the wires 23a extend become equal to each other. The wires 23a are made of, for example, copper or copper foil, and printed on the FPC 23.

The lead wires 24 include conductive wires made of metal, and coatings that are made of insulating material, such as rubber, and disposed on outer peripheries of the conductive wires. As illustrated in FIG. 3, the lead wires 24 are collectively arranged on the proximal end side. The lead wires 24 are arranged such that, in a plane perpendicular to a distal end of the ultrasound endoscope 1, a region in which centers of the piezoelectric elements 21 arranged in a circumferential manner and the lead wires 24 are connected does not cross a direction in which the ultrasound endoscope 1 is bent.

The ultrasound transducer 2 configured as described above applies ultrasound waves to an observation target via the acoustic lens 111a when the piezoelectric elements 21 vibrate in response to input of pulse signals. Further, ultrasound waves reflected from the observation target are transmitted to the piezoelectric elements 21 via the acoustic lens 111a. The piezoelectric elements 21 vibrate in response to the transmitted ultrasound waves, and the piezoelectric elements 21 convert the vibration into electrical echo signals and output them as echo signals to the ultrasound observation device.

Figure 5:
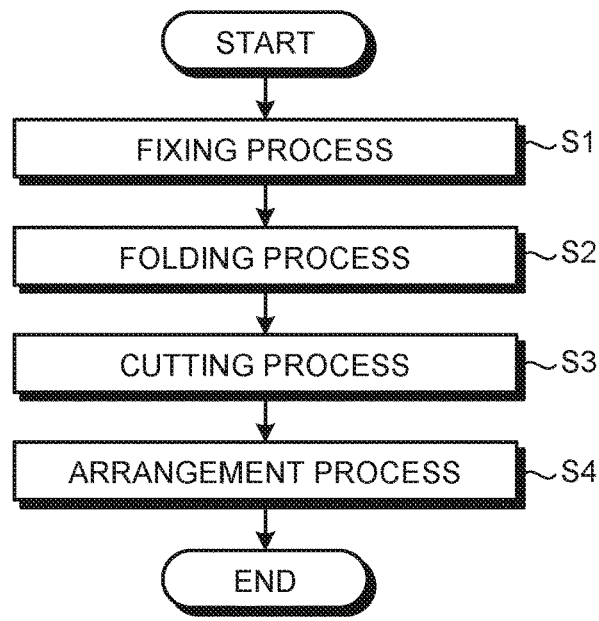
FIG. 5 is a flowchart illustrating a process of manufacturing the ultrasound transducer illustrated in FIG. 2.
Figure 6:
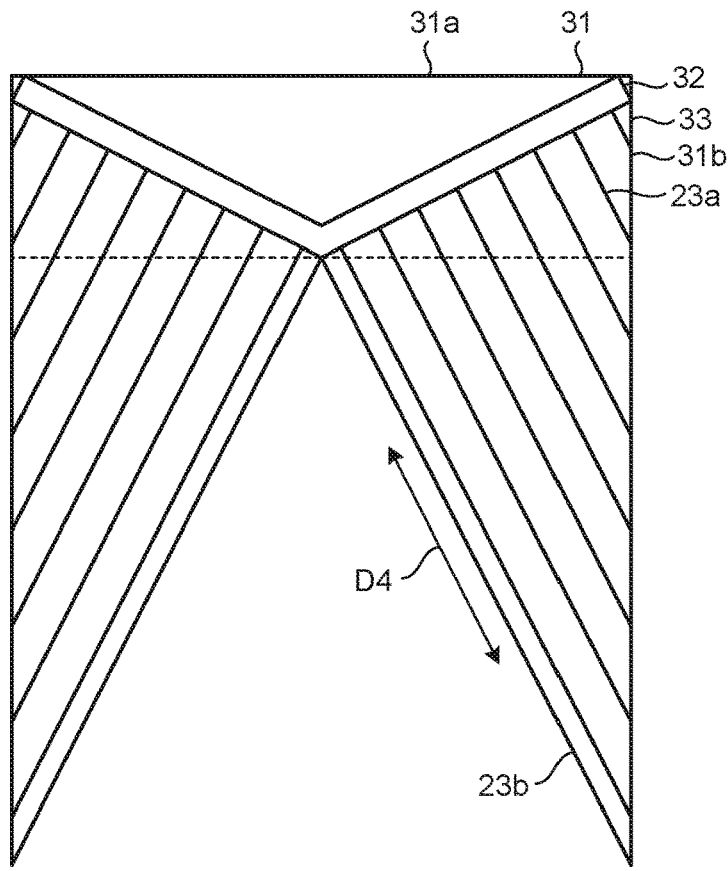
FIG. 6 is a diagram for explaining a fixing process illustrated in FIG. 5.

FIG. 5 is a flowchart illustrating a process of manufacturing the ultrasound transducer illustrated in FIG. 2. FIG. 6 is a diagram for explaining a fixing process illustrated in FIG. 5. As illustrated in FIG. 6, first, a conductive electrode member 32 is laminated on a plate-like piezoelectric material 31, and a substrate member 33 is fixed on a proximal end side of the electrode member 32 such that the substrate member 33 includes the plurality of wires 23a, which are electrically connected to the electrode member 32 and extend along the direction D4 crossing a long side 31a of the piezoelectric material 31, and the hypotenuse 23b, which obliquely extends from the proximal end side along the direction D4 crossing the long side 31a (Step S1: fixing process). Specifically, by soldering the electrode member 32 and the wires 23a, the substrate member 33 is fixed to the proximal end side of the electrode member 32.

Figure 7:
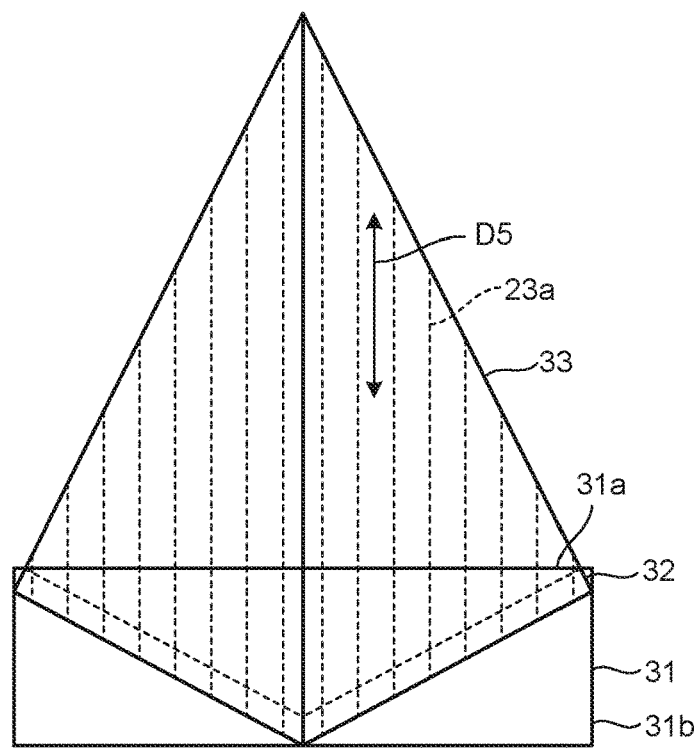
FIG. 7 is a diagram for explaining a folding process illustrated in FIG. 5.

FIG. 7 is a diagram for explaining a folding process illustrated in FIG. 5. As illustrated in FIG. 7, the substrate member 33 is folded such that a direction D5 along which the wires 23a extend and a short side 31b of the piezoelectric material 31 become parallel to each other (Step S2: folding process).

Figure 8:
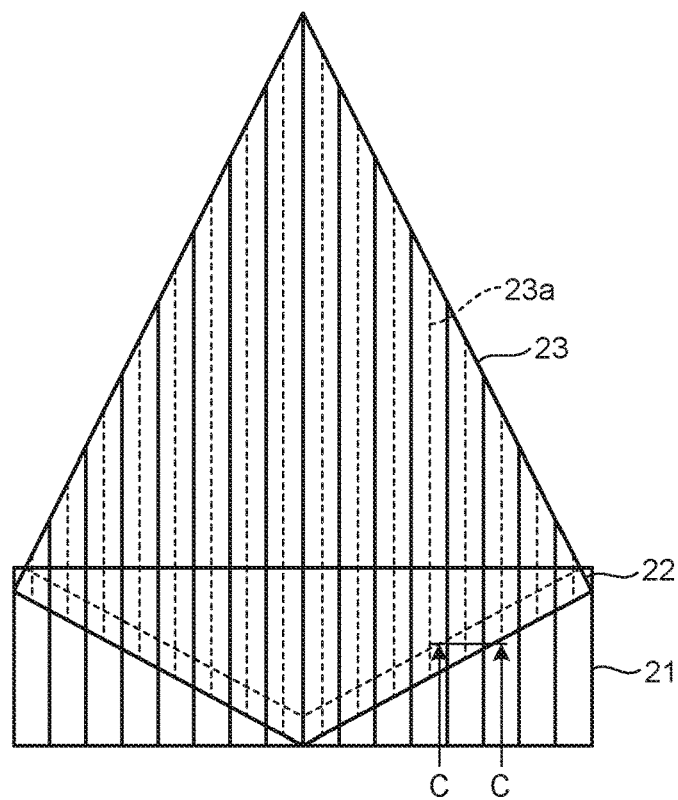
FIG. 8 is a diagram for explaining a cutting process illustrated in FIG. 5.

FIG. 8 is a diagram for explaining a cutting process illustrated in FIG. 5. As illustrated in FIG. 8, the piezoelectric material 31, the electrode member 32, and the substrate member 33 are cut while the substrate member 33 is folded (Step S3: cutting process).

Figure 9:
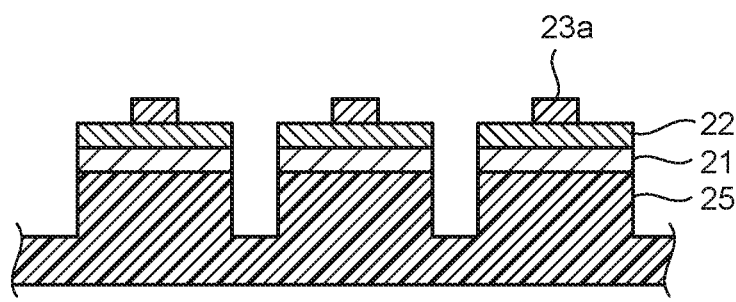
FIG. 9 is a diagram illustrating cross sections of cut piezoelectric elements.

FIG. 9 is a diagram illustrating cross sections of cut piezoelectric elements. FIG. 9 illustrates the cross sections taken along a line C-C in FIG. 8, but the FPC 23 is not illustrated in FIG. 9. As illustrated in FIG. 9, connection members 25 made of resin or the like are arranged on back surfaces of the piezoelectric elements 21 and connect the adjacent piezoelectric elements 21. The connection members 25 may have a function as an acoustic matching layer that matches acoustic impedance between the piezoelectric elements 21 and the observation target in order to effectively transmit sounds (ultrasound waves) between the piezoelectric elements 21 and the observation target.

Thereafter, the FPC 23 obtained by cutting the substrate member 33 is folded back to a non-folded position from the folded state, so that the state as illustrated in FIG. 4 is obtained. Further, the plurality of piezoelectric elements 21 obtained by cutting the piezoelectric material 31, the plurality of electrodes 22 obtained by cutting the electrode member 32, and the FPC 23 are arranged in a circumferential manner such that the piezoelectric elements 21 are arranged on the outer side (Step S4: arrangement process). As a result, the radial type ultrasound transducer 2 as illustrated in FIG. 2 and FIG. 3 is manufactured.

According to the embodiment, as illustrated in FIG. 2 and FIG. 3, the FPC 23 has the hypotenuse 23b and a portion in which the FPC 23 protrudes from the distal end rigid portion 111 has flexibility, a length of a portion that is not bendable due to the FPC 23 is increased. Therefore, a length of a non-bendable portion in the ultrasound transducer 2 is reduced.

Meanwhile, to increase the bendability, it may be possible to provide a structure, such as a slit, a clearance groove, or bellows, on the proximal end side of the FPC 23.

In addition, according to the embodiment, the lead wires 24 are collectively arranged on the proximal end side, so that it is possible to easily handle the lead wires 24. Further, the lead wires 24 are arranged such that, in the plane perpendicular to the distal end of the ultrasound endoscope 1, the region in which the centers of the piezoelectric elements 21 arranged in a circumferential manner and the lead wires 24 are connected does not cross the direction in which the ultrasound endoscope 1 is bent, so that it is possible to prevent the collected lead wires 24 from interfering with bending operation.

First Modification

Figure 10:
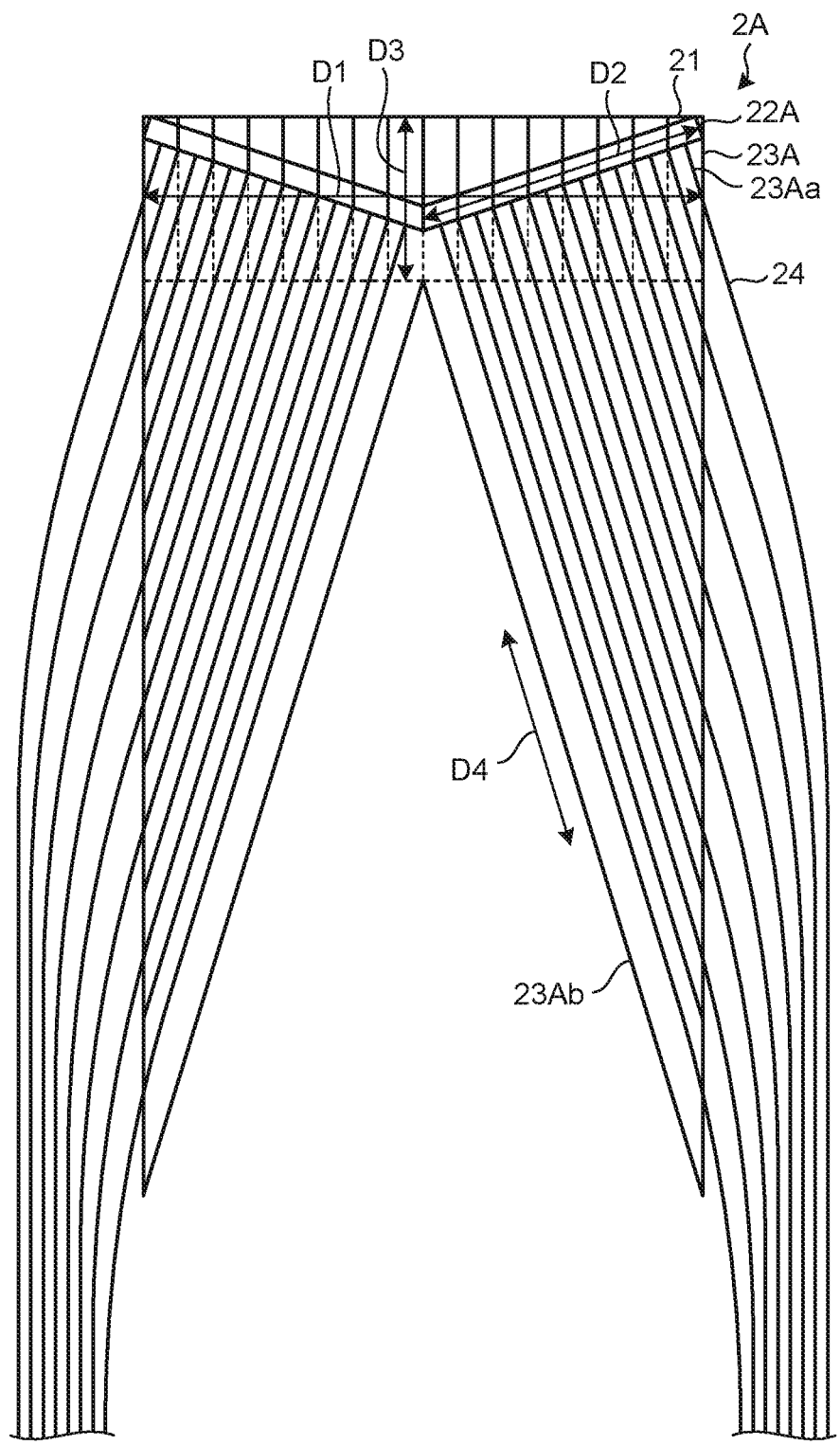
FIG. 10 is a diagram illustrating a state before an ultrasound transducer according to a first modification is arranged in a circumferential manner.

FIG. 10 is a diagram illustrating a state before an ultrasound transducer according to a first modification is arranged in a circumferential manner. As illustrated in FIG. 10, an ultrasound transducer 2A includes the piezoelectric elements 21, electrodes 22A, wires 23Aa that extend along the direction D4 crossing the direction D3, an FPC 23A that is entirely integrated into a single piece and has a hypotenuse 23Ab obliquely extending from a proximal end side along the direction D4 crossing the direction D3, and the lead wires 24.

According to the first modification, because the FPC 23A has the hypotenuse 23Ab, a portion in which the FPC 23A protrudes from the distal end rigid portion 111 has flexibility, so that a length of a non-bendable portion is reduced. Further, because the FPC 23A is entirely integrated into a single piece, it is possible to simplify the manufacturing process as compared to a case in which an FPC is separated into a plurality of pieces.

Second Modification

Figure 11:
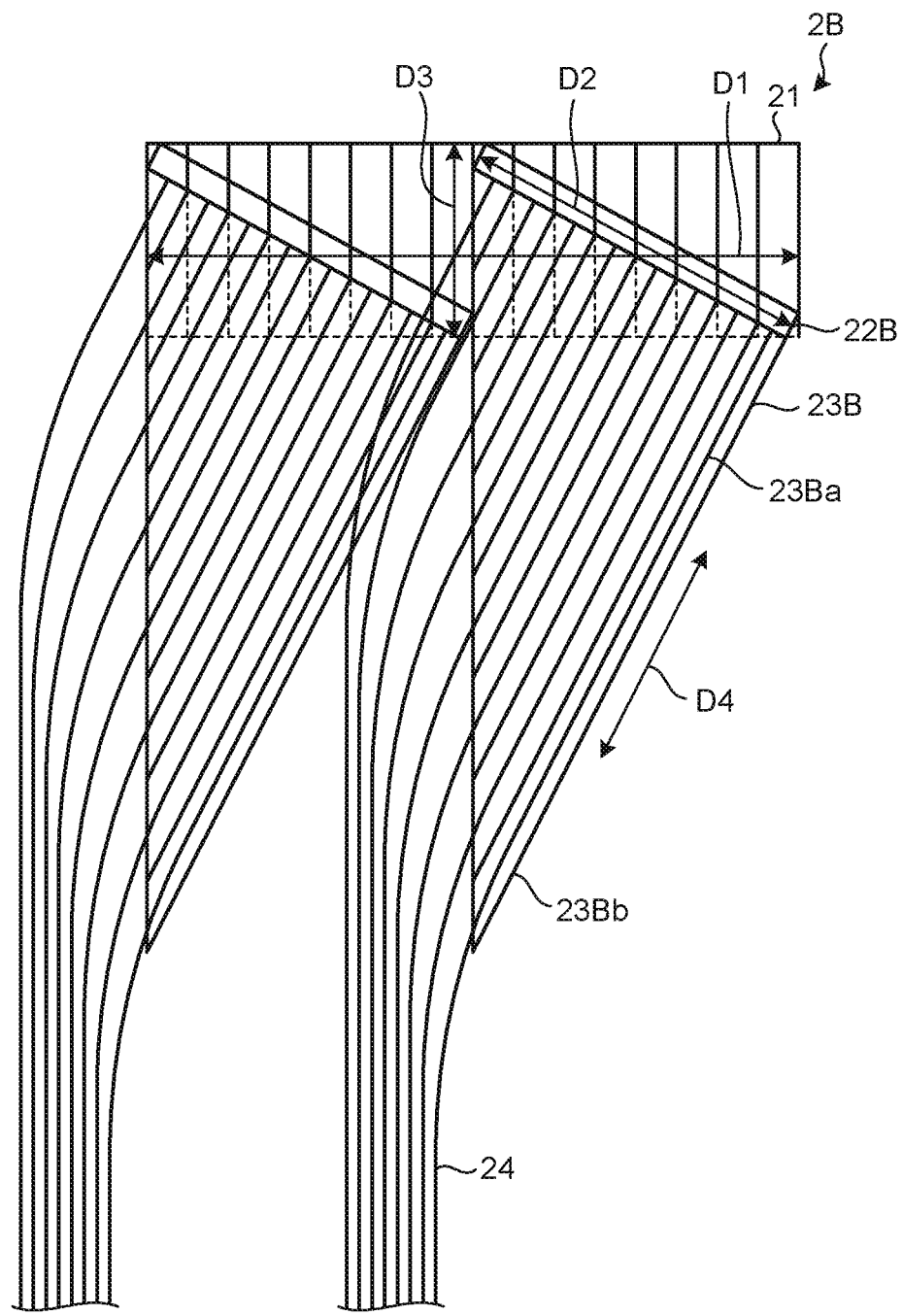
FIG. 11 is a diagram illustrating a state before an ultrasound transducer according to a second modification is arranged in a circumferential manner.

FIG. 11 is a diagram illustrating a state before an ultrasound transducer according to a second modification is arranged in a circumferential manner. As illustrated in FIG. 11, an ultrasound transducer 2B includes the piezoelectric elements 21, electrodes 22B, wires 23Ba that extend along the direction D4 crossing the direction D3, two FPCs 23B that have the same shape, that are arranged side by side, and that have hypotenuses 23Bb obliquely extending from proximal end sides along the direction D4 crossing the direction D3, and the lead wires 24.

According to the second modification, because the two FPCs 23B have the hypotenuses 23B*b*, a portion in which each of the two FPCs 23B protrudes from the distal end rigid portion 111 has flexibility, so that a length of a non-bendable portion is reduced. Further, because the two FPCs 23B have the same shape, it is possible to reduce the number of components as compared to a case in which a plurality of FPCs having different shapes are prepared.

Furthermore, even in the second modification, it is preferable that the lead wires 24 are arranged such that, in the plane perpendicular to the distal end of the ultrasound endoscope 1, the region in which the centers of the piezoelectric elements 21 arranged in a circumferential manner and the lead wires 24 are connected does not cross the direction in which the ultrasound endoscope 1 is bent. Specifically, it is sufficient that two directions along which the lead wires 24 that are collected with respect to the centers of the piezoelectric elements 21 arranged in a circumferential manner extend and the direction in which the insertion portion 11 is bent are shifted by 45°. In this case, it is possible to prevent the collected lead wires 24 form interfering with bending operation.

Third Modification

Figure 12:
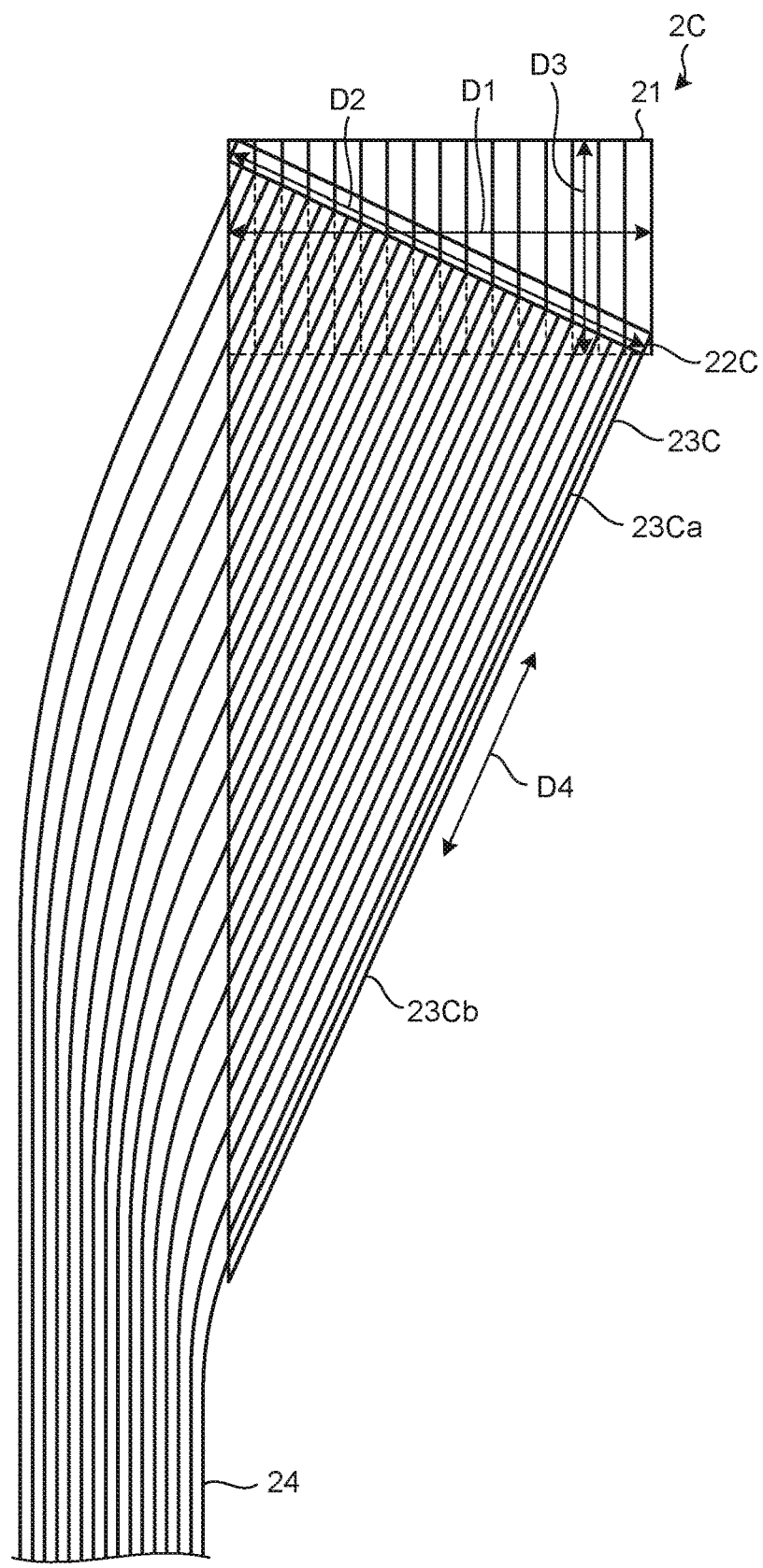
FIG. 12 is a diagram illustrating a state before an ultrasound transducer according to a third modification is arranged in a circumferential manner.

FIG. 12 is a diagram illustrating a state before an ultrasound transducer according to a third modification is arranged in a circumferential manner. As illustrated in FIG. 12, an ultrasound transducer 2C includes the piezoelectric elements 21, electrodes 22C that are arranged on diagonal lines of the piezoelectric elements 21, wires 23Ca that extend along the direction D4 crossing the direction D3, an FPC 23C that is entirely integrated into a single piece and that has a hypotenuse 23Cb obliquely extending from a proximal end side along the direction D4 crossing the direction D3, and the lead wires 24.

According to the third modification, because the FPC 23C has the hypotenuse 23Cb, a portion in which the FPC 23C protrudes from the distal end rigid portion 111 has flexibility, so that a length of a non-bendable portion is reduced. Further, because the FPC 23C is entirely integrated into a single piece, it is possible to simplify the manufacturing process as compared to a case in which an FPC is separated into a plurality of pieces.

Fourth Modification

Figure 13:
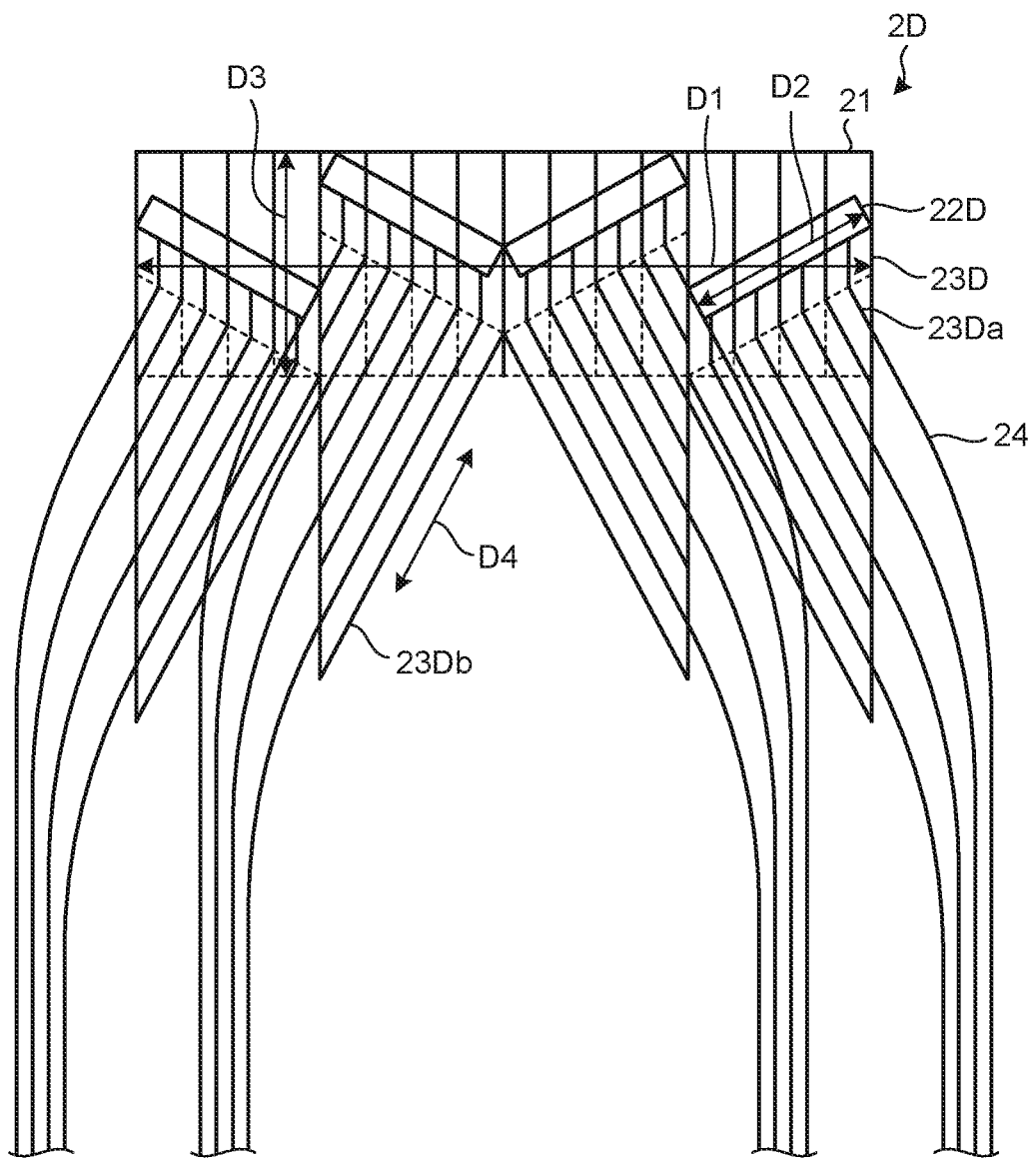
FIG. 13 is a diagram illustrating a state before an ultrasound transducer according to a fourth modification is arranged in a circumferential manner.

FIG. 13 is a diagram illustrating a state before an ultrasound transducer according to a fourth modification is arranged in a circumferential manner. As illustrated in FIG. 13, an ultrasound transducer 2D includes the piezoelectric elements 21, electrodes 22D, wires 23Da that extend along the direction D4 crossing the direction D3, and four FPCs 23D that have hypotenuses 23Db obliquely extending from proximal end sides along the direction D4 crossing the direction D3, and the lead wires 24.

According to the fourth modification, because the four FPCs 23D have the hypotenuses 23Db, a portion in which each of the four the FPCs 23B protrudes from the distal end rigid portion 111 has flexibility, so that a length of a non-bendable portion is reduced.

Further, even in the fourth modification, similarly to the second modification, it is preferable to arrange the lead wires 24 such that four directions along which the lead wires 24 that are collected with respect to the centers of the piezoelectric elements 21 arranged in a circumferential manner extend and the direction in which the insertion portion 11 is bent are shifted by 45°. Meanwhile, the direction in which the insertion portion 11 is bent may be, for example, one direction, two directions, or four directions. Even if the direction in which the insertion portion 11 is bent is four directions, it is possible to prevent interference with bending operation in each of the directions by shifting each of the four directions along which the collected lead wires 24 extend and each of the four direction in which the insertion portion 11 is bent by 45°.

Fifth Modification

Figure 14:
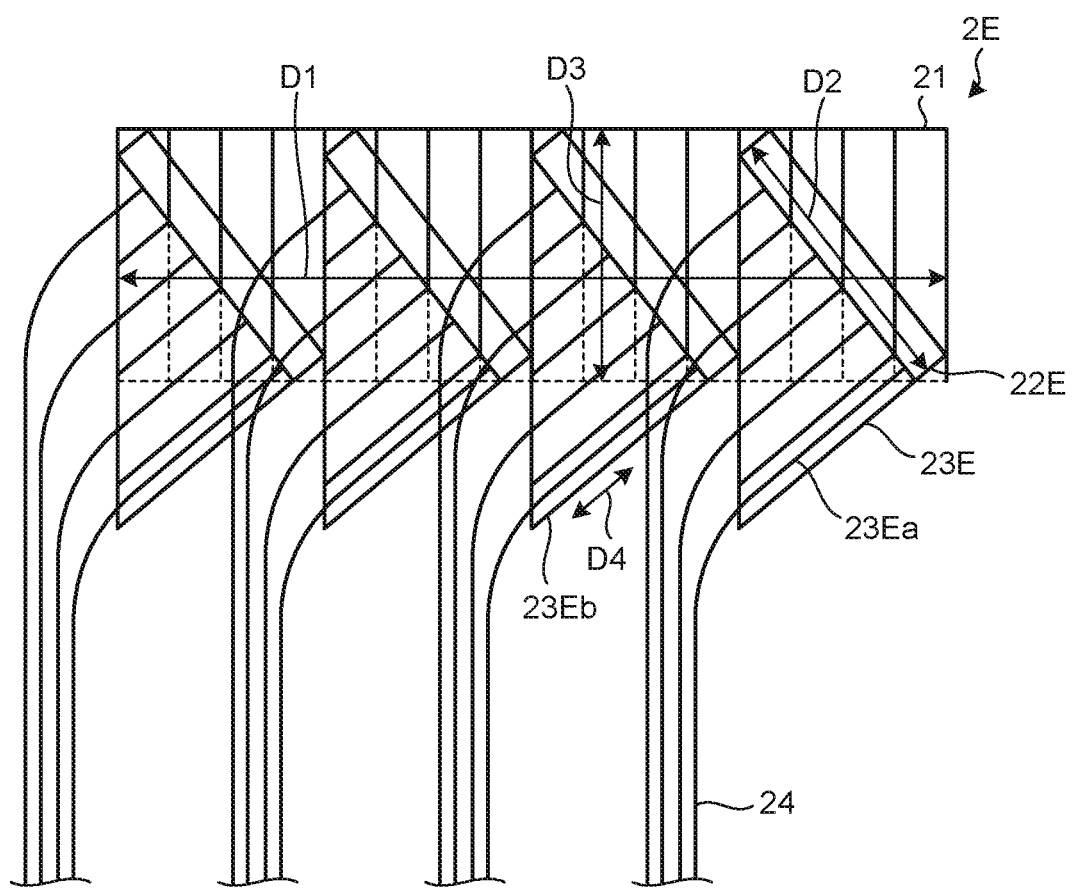
FIG. 14 is a diagram illustrating a state before an ultrasound transducer according to a fifth modification is arranged in a circumferential manner.

FIG. 14 is a diagram illustrating a state before an ultrasound transducer according to a fifth modification is arranged in a circumferential manner. As illustrated in FIG. 14, an ultrasound transducer 2E includes the piezoelectric elements 21, electrodes 22E, wires 23Ea that extend along the direction D4 crossing the direction D3, four FPCs 23E that have hypotenuses 23Eb obliquely extending from proximal end sides along the direction D4 crossing the direction D3, and the lead wires 24.

According to the fifth modification, because the four FPCs 23E have the hypotenuses 23Eb, a portion in which each of the four FPCs 23E protrudes from the distal end rigid portion 111 has flexibility, so that a length of a non-bendable portion is reduced.

Further, even in the fifth modification, similarly to the second modification, it is preferable to arrange the lead wires 24 such that four directions along which the lead wires 24 that are collected with respect to the centers of the piezoelectric elements 21 arranged in a circumferential manner extend and the direction in which the insertion portion 11 is bent are shifted by 45°.

Sixth Modification

Figure 15:
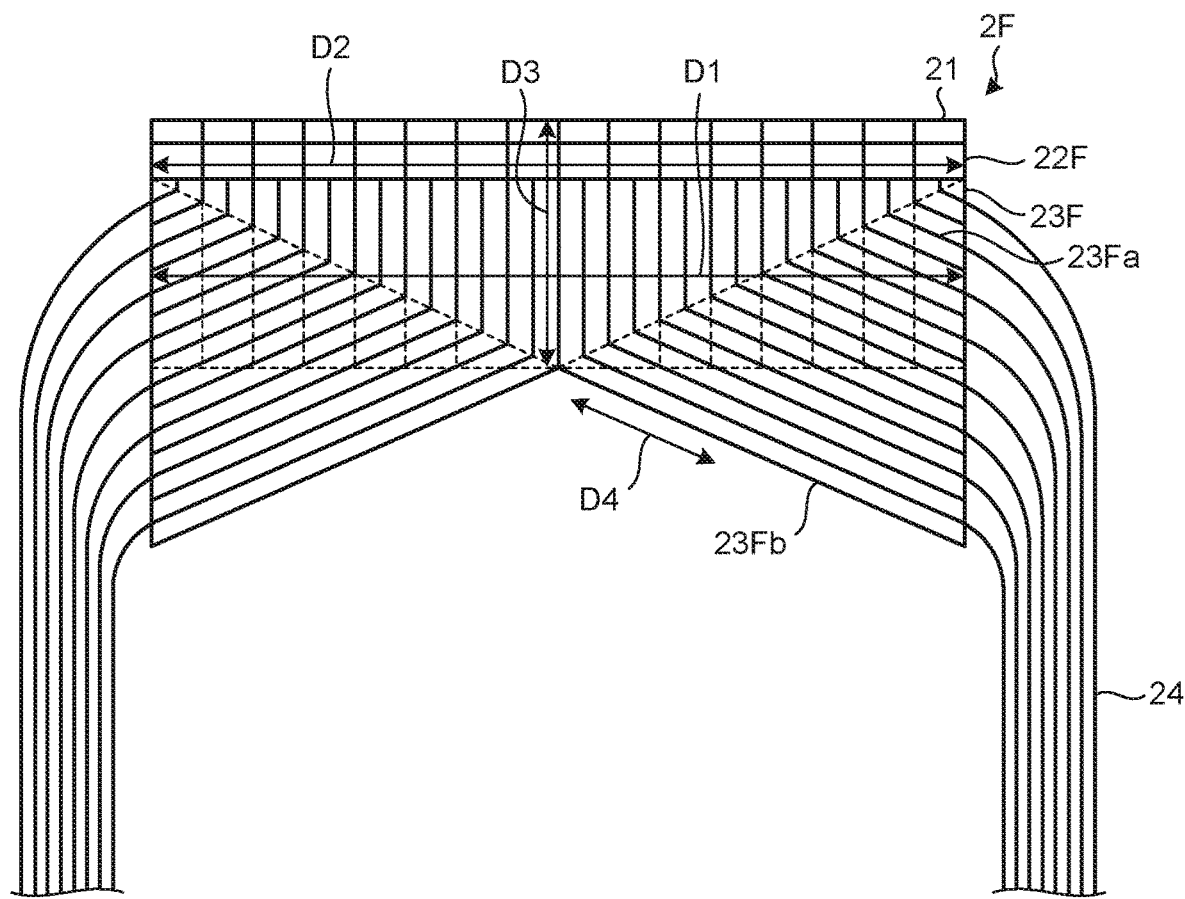
FIG. 15 is a diagram illustrating a state before an ultrasound transducer according to a sixth modification is arranged in a circumferential manner.

FIG. 15 is a diagram illustrating a state before an ultrasound transducer according to a sixth modification is arranged in a circumferential manner. As illustrated in FIG. 15, an ultrasound transducer 2F includes the piezoelectric elements 21, electrodes 22F, wires 23Fa, some parts of which extend along the direction D4 crossing the direction D3 and other parts of which extend along the direction D3 perpendicular to the arrangement direction D1 of the piezoelectric elements 21, an FPC 23F that has a hypotenuse 23Fb obliquely extending from a proximal end side along the direction D4 crossing the direction D3, and the lead wires 24.

According to the sixth modification, because the two FPCs 23F have the hypotenuses 23Fb, a portion in which each of the two FPCs 23F protrudes from the distal end rigid portion 111 has flexibility, so that a length of a non-bendable portion is reduced. In this manner, it may be possible to arrange some parts of the wires along the direction D3 perpendicular to the arrangement direction D1 of the piezoelectric elements. Further, it may be possible to arrange the electrodes along the direction D2 that extends along the arrangement direction D1 of the piezoelectric elements.

According to the present disclosure, it is possible to realize an ultrasound transducer, an ultrasound endoscope, and a method of manufacturing the ultrasound transducer such that a length of a non-bendable portion of a radial type ultrasound transducer used in an ultrasound endoscope having a bendable distal end is reduced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion portion for use with an ultrasound endoscope, the insertion portion comprising:
a bending portion on a distal end side of an insertion portion;
a radial type ultrasound transducer arranged distally relative to the bending portion, the ultrasound transducer comprising:
a plurality of piezoelectric elements arranged at predetermined intervals in a circumferential direction and configured to transmit and receive ultrasound waves; and
a plurality of electrodes arranged in the respective piezoelectric elements at an electrode direction offset at an angle from the circumferential direction such that the electrode direction is different from the circumferential direction; and
a flexible printed circuit electrically connected to each of the electrodes,
wherein the flexible printed circuit includes a plurality of wires, at least parts of the plurality of wires extend in a wire direction perpendicular to the electrode direction,
the plurality of wires are electrically connected to the respective electrodes of the piezoelectric elements at positions where at least parts of the wires cross a longitudinal direction of the bending portion.

2. The insertion portion according to claim 1, wherein the angle between the electrode direction and the longitudinal direction and an angle between the electrode direction and the wire direction are equal to each other.

3. The insertion portion according to claim 1 further comprising:

a plurality of lead wires electrically connected to the respective wires, wherein
the plurality of lead wires are collectively arranged in a bundle on a proximal end side of the ultrasound transducer.

4. An ultrasound endoscope comprising:
the insertion portion according to claim 1;
a distal end rigid portion made of a rigid member arranged on a distal end of the bending portion; and
an operating unit arranged on a proximal end side of the insertion portion for operating the bending portion.

5. An insertion portion for use with an ultrasound endoscope, the insertion portion comprising:
a bending portion on a distal end side of an insertion portion;
a radial type ultrasound transducer arranged distally relative to the bending portion, the ultrasound transducer comprising:
a plurality of piezoelectric elements arranged at predetermined intervals in a circumferential direction and transmit and receive ultrasound waves; and
a plurality of electrodes arranged in the respective piezoelectric elements; and
a flexible printed circuit electrically connected to each of the electrodes,
wherein the plurality of electrodes having a respective plurality of connection positions for connecting to the flexible printed circuit, an arrangement direction of the plurality of connection positions is inclined relative to the circumferential direction.

6. The insertion portion according to claim 1, wherein the flexible printed circuit is disposed at least partially in the bending portion.

7. The insertion portion according to claim 5, wherein the flexible printed circuit is at least partially disposed in the bending portion.

8. The insertion portion according to claim 1, wherein at least a portion of the plurality of wires immediately adjacent to the plurality of electrodes extend so as to cross the longitudinal direction.

9. The insertion portion according to claim 1, wherein the plurality of wires comprise:
a proximal portion where the plurality of wires are gathered together and extend in the longitudinal direction; and
a distal portion where the plurality of wires extend from a distal end of the proximal portion and are spaced apart in the circumferential manner, the plurality of wires in the distal portion extending such that all portions of the spaced wires from the distal end of the proximal portion to the plurality of electrodes cross the longitudinal direction.

10. The insertion portion according to claim 5, wherein the flexible printed circuit comprises a plurality of wires electrically connected to the respective plurality of electrodes, at least a portion of the plurality of wires immediately adjacent to the plurality of electrodes extend so as to be inclined with respect to a longitudinal direction of the bending portion.

11. The insertion portion according to claim 5, wherein the plurality of wires comprising:
a proximal portion where the plurality of wires are gathered together and extend in the longitudinal direction; and
a distal portion where the plurality of wires extend from a distal end of the proximal portion and are spaced apart in the circumferential manner, the plurality of wires in the distal portion extending such that all portions of the spaced wires from the distal end of the proximal portion to the plurality of electrodes are inclined with respect to a longitudinal direction of the bending portion.

* * * * *